United States Patent
Burkhart et al.

(10) Patent No.: US 11,844,512 B2
(45) Date of Patent: *Dec. 19, 2023

(54) SUTURE ANCHOR FOR KNOTLESS FIXATION OF TISSUE

(71) Applicant: Arthrex, Inc., Naples, FL (US)

(72) Inventors: Stephen S. Burkhart, Boerne, TX (US); Peter J. Dreyfuss, Naples, FL (US); Neil S. ElAttrache, Los Angeles, CA (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/975,321

(22) Filed: Oct. 27, 2022

(65) Prior Publication Data

US 2023/0048745 A1 Feb. 16, 2023

Related U.S. Application Data

(63) Continuation of application No. 15/976,157, filed on May 10, 2018, now Pat. No. 11,571,200, which is a (Continued)

(51) Int. Cl.
*A61B 17/04* (2006.01)
*A61F 2/08* (2006.01)

(52) U.S. Cl.
CPC ........ *A61B 17/0401* (2013.01); *A61F 2/0805* (2013.01); *A61F 2/0811* (2013.01);
(Continued)

(58) Field of Classification Search
CPC ........ A61B 2017/0409; A61B 17/0401; A61B 2017/044; A61B 2017/049;
(Continued)

(56) References Cited

U.S. PATENT DOCUMENTS 4,484,570 A 11/1984 Sutter et al.
4,632,100 A 12/1986 Somers et al.
(Continued)

FOREIGN PATENT DOCUMENTS

EP 1 857 054 A2 11/2007
WO WO 02/21999 A2 3/2002
(Continued)

OTHER PUBLICATIONS

Petition for Inter Partes Review (IPR) of U.S. Pat. No. 9,179,907 (Case No. IPR 2017-00275).
(Continued)

*Primary Examiner* — Diane D Yabut
*Assistant Examiner* — Christina C Lauer
(74) *Attorney, Agent, or Firm* — BLANK ROME LLP

(57) ABSTRACT

A suture anchor for knotless fixation of tissue. The suture anchor includes an implant configured to hold a suture to be anchored in bone without requiring suture knots. The suture is secured in bone by inserting the implant holding the suture into a hole in the bone, and advancing a fixation device, such as a cannulated interference screw, over a shaft at the proximal end of the implant.

22 Claims, 11 Drawing Sheets

Related U.S. Application Data continuation of application No. 14/707,861, filed on May 8, 2015, now Pat. No. 10,881,388, which is a continuation of application No. 13/403,366, filed on Feb. 23, 2012, now abandoned, which is a continuation of application No. 12/418,391, filed on Apr. 3, 2009, now abandoned, which is a continuation-in-part of application No. 12/368,946, filed on Feb. 10, 2009, now abandoned, which is a continuation-in-part of application No. 12/043,008, filed on Mar. 5, 2008, now abandoned, which is a continuation-in-part of application No. 11/802,057, filed on May 18, 2007, now Pat. No. 9,005,246, said application No. 12/368,946 is a continuation-in-part of application No. 11/392,798, filed on Mar. 30, 2006, now Pat. No. 7,803,173.

(60) Provisional application No. 60/801,097, filed on May 18, 2006, provisional application No. 60/666,518, filed on Mar. 30, 2005.

(52) U.S. Cl.
CPC . *A61B 2017/044* (2013.01); *A61B 2017/0409* (2013.01); *A61B 2017/0414* (2013.01); *A61B 2017/0438* (2013.01); *A61B 2017/0445* (2013.01); *A61B 2017/0458* (2013.01); *A61B 2017/0459* (2013.01); *A61F 2002/0817* (2013.01); *A61F 2002/0841* (2013.01); *A61F 2002/0852* (2013.01); *A61F 2002/0858* (2013.01); *A61F 2002/0888* (2013.01)

(58) Field of Classification Search
CPC .... A61B 2017/0445; A61B 2017/0458; A61B 2017/0459; A61B 2017/0414
See application file for complete search history.

(56) References Cited

U.S. PATENT DOCUMENTS

| | | | |
|---|---|---|---|
| 4,870,957 A | 10/1989 | Goble | |
| 5,084,050 A | 1/1992 | Draenert | |
| 5,129,904 A | 7/1992 | Illi | |
| 5,152,790 A | 10/1992 | Rosenberg et al. | |
| 5,236,445 A | 8/1993 | Hayhurst | |
| 5,249,899 A | 10/1993 | Wilson | |
| 5,258,016 A | 11/1993 | DiPoto | |
| 5,368,595 A | 11/1994 | Lewis | |
| 5,423,860 A | 6/1995 | Lizardi et al. | |
| 5,500,000 A | 3/1996 | Feagin et al. | |
| 5,540,718 A | 7/1996 | Bartlett | |
| 5,545,180 A | 8/1996 | Le et al. | |
| 5,584,835 A | 12/1996 | Greenfield | |
| 5,827,285 A | 10/1998 | Bramlet | |
| 5,860,973 A | 1/1999 | Michelson | |
| 5,891,168 A | 4/1999 | Thal | |
| 5,935,129 A | 8/1999 | McDevitt | |
| 5,968,047 A | 10/1999 | Reed | |
| 6,045,574 A | 4/2000 | Thal | |
| 6,048,343 A | 4/2000 | Mathis et al. | |
| 6,143,017 A | 11/2000 | Thal | |
| 6,214,007 B1 | 4/2001 | Anderson | |
| 6,355,043 B1 | 3/2002 | Adam | |
| 6,368,326 B1 | 4/2002 | Dakin | |
| 6,517,542 B1 | 2/2003 | Papay et al. | |
| 6,527,794 B1 | 3/2003 | McDevitt et al. | |
| 6,544,281 B2 | 4/2003 | ElAttrache et al. | |
| 6,554,281 B2 | 4/2003 | Flannery | |
| 6,589,245 B1 | 7/2003 | Weiler et al. | |
| 6,840,953 B2 | 1/2005 | Martinek | |
| 6,863,671 B1 | 3/2005 | Strobel et al. | |
| 6,939,135 B2 | 9/2005 | Sapian | |
| 7,037,324 B2 | 5/2006 | Martinek | |
| 7,083,637 B1 | 8/2006 | Tannhauser | |
| 7,083,647 B1 | 8/2006 | Sklar et al. | |
| 7,261,716 B2 | 8/2007 | Strobel et al. | |
| 7,300,439 B2 | 11/2007 | May | |
| 7,329,272 B2 | 2/2008 | Burkhart et al. | |
| 7,572,283 B1 | 8/2009 | Meridew | |
| 7,585,311 B2 | 9/2009 | Green et al. | |
| 7,588,587 B2 | 9/2009 | Barbieri et al. | |
| 7,645,293 B2 | 1/2010 | Martinek et al. | |
| 7,717,947 B1 | 5/2010 | Wilberg et al. | |
| 7,803,173 B2 | 9/2010 | Burkhart et al. | |
| 7,976,565 B1* | 7/2011 | Meridew | A61B 17/0401 606/1 |
| 7,981,140 B2 | 7/2011 | Burkhart | |
| 7,993,369 B2 | 8/2011 | Dreyfuss | |
| 8,012,174 B2 | 9/2011 | ElAttrache et al. | |
| 8,100,942 B1 | 1/2012 | Green | |
| 8,109,969 B1 | 2/2012 | Green | |
| 8,114,127 B2 | 2/2012 | West, Jr. | |
| 8,663,279 B2 | 3/2014 | Burkhart et al. | |
| 9,005,246 B2 | 4/2015 | Burkhart et al. | |
| 10,881,388 B2* | 1/2021 | Burkhart | A61B 17/0401 |
| 11,571,200 B2* | 2/2023 | Burkhart | A61F 2/0805 |
| 2002/0013608 A1* | 1/2002 | ElAttrache | A61F 2/0811 606/232 |
| 2002/0147463 A1 | 10/2002 | Martinek | |
| 2002/0156476 A1 | 10/2002 | Wilford | |
| 2003/0065332 A1 | 4/2003 | TenHuisen | |
| 2003/0125739 A1 | 7/2003 | Bagga et al. | |
| 2003/0153947 A1 | 8/2003 | Koseki | |
| 2004/0093030 A1 | 5/2004 | Cox et al. | |
| 2004/0093031 A1 | 5/2004 | Burkhart et al. | |
| 2004/0138706 A1 | 7/2004 | Abrams | |
| 2004/0193217 A1 | 9/2004 | Lubbers et al. | |
| 2004/0225292 A1 | 11/2004 | Sasso et al. | |
| 2005/0089552 A1 | 4/2005 | Altman et al. | |
| 2005/0119698 A1 | 6/2005 | Martinek | |
| 2006/0004364 A1 | 1/2006 | Green et al. | |
| 2006/0074422 A1 | 4/2006 | Story et al. | |
| 2006/0079904 A1 | 4/2006 | Thal | |
| 2006/0100630 A1 | 5/2006 | West, Jr. | |
| 2006/0235413 A1 | 10/2006 | Denham et al. | |
| 2006/0247642 A1 | 11/2006 | Stone et al. | |
| 2006/0259076 A1 | 11/2006 | Burkhart et al. | |
| 2007/0038221 A1 | 2/2007 | Fine et al. | |
| 2007/0060922 A1 | 3/2007 | Dreyfuss | |
| 2007/0135843 A1 | 6/2007 | Burkhart | |
| 2007/0191849 A1 | 8/2007 | ElAttrache | |
| 2007/0225719 A1 | 9/2007 | Stone et al. | |
| 2008/0004659 A1 | 1/2008 | Burkhart et al. | |
| 2008/0009904 A1 | 1/2008 | Bourque et al. | |
| 2008/0154314 A1 | 6/2008 | McDevitt | |
| 2008/0208253 A1 | 8/2008 | Dreyfuss et al. | |
| 2008/0215091 A1 | 9/2008 | Dreyfuss | |
| 2008/0275431 A1 | 11/2008 | Stone et al. | |
| 2008/0281325 A1 | 11/2008 | Stone et al. | |
| 2009/0192546 A1 | 7/2009 | Schmieding et al. | |
| 2009/0281581 A1 | 11/2009 | Berg | |
| 2009/0287259 A1 | 11/2009 | Trenhaile | |
| 2010/0248888 A1 | 9/2010 | Hamperl | |
| 2010/0249854 A1 | 9/2010 | Thomas | |
| 2010/0331896 A1 | 12/2010 | Le Couedic et al. | |
| 2011/0106252 A1 | 5/2011 | Barwood | |
| 2011/0313455 A1 | 12/2011 | ElAttrache et al. | |
| 2012/0022588 A1 | 1/2012 | Berg | |
| 2012/0165868 A1 | 6/2012 | Burkhart et al. | |
| 2013/0035721 A1 | 2/2013 | Brunelle | |
| 2013/0158597 A1 | 6/2013 | Hernandez | |
| 2013/0345750 A1 | 12/2013 | Sullivan | |
| 2014/0364906 A1 | 12/2014 | Palese | |
| 2017/0209139 A1 | 7/2017 | Burkhart | |

FOREIGN PATENT DOCUMENTS

| | | |
|---|---|---|
| WO | WO 2006/060035 A2 | 6/2006 |
| WO | WO 2006/099109 A2 | 9/2006 |

(56) References Cited

FOREIGN PATENT DOCUMENTS

OTHER PUBLICATIONS

Claim Construction Memorandum and Order, *Arthrex, Inc.* v. *Smith & Nephew, Inc et al.,* Case No. 2:15-cv-01047 (RSP) (E.D. Texas Aug. 10, 2016).
Letter from Celia M. Witten, M.D., to Edward F. Kent, Re: K974345 (Feb. 13, 1998).
Letter from Celia M. Witten, M.D., to Mark Ritchart, Re: K012125 (Sep. 17, 2001).
Declaration of Dr. David R. McAllister.
Aaron T. Hecker et al., "Pull-out Strength of Suture Anchors for Rotator Cuff and Bankart Lesion Repairs," American Journal of Sports Medicine, vol. 21, No. 6, 874-879 (1993).
F. Alan Barber et al., "Suture Anchor Failure Strength—An In Vivo Study," *Arthroscopy: the Journal of Arthroscopic and Related Surgery,* vol. 9, No. 6, 647-652 at 647 (1993).
F. Alan Barber et al., "Suture Anchor Strength Revisited," *Arthroscopy: the Journal of Arthroscopic and Related Surgery,* vol. 12, No. 1, 32-38 (1996).
F. Alan Barber et al., "Suture Anchors—Update 1999," *Arthroscopy: the Journal of Arthroscopic and Related Surgery,* vol. 15, No. 5, 719-725 (1999).

\* cited by examiner

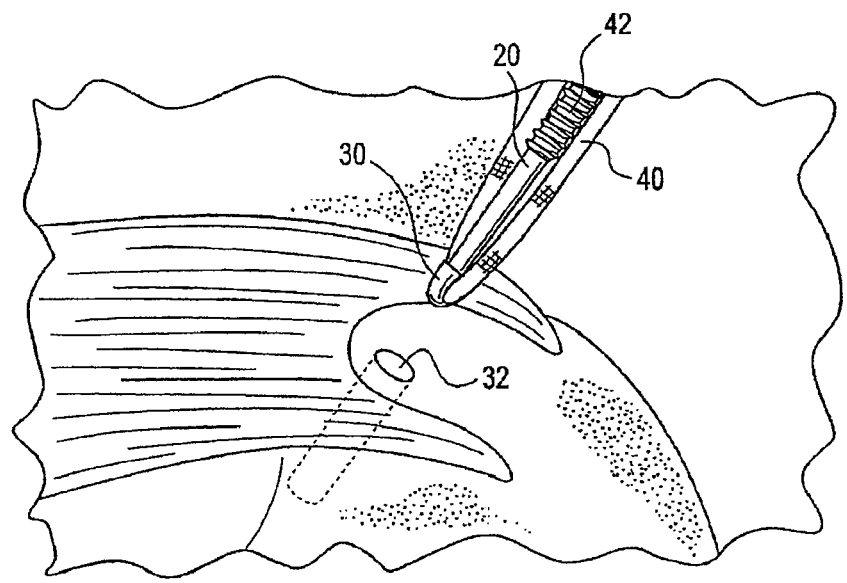
FIG. 3
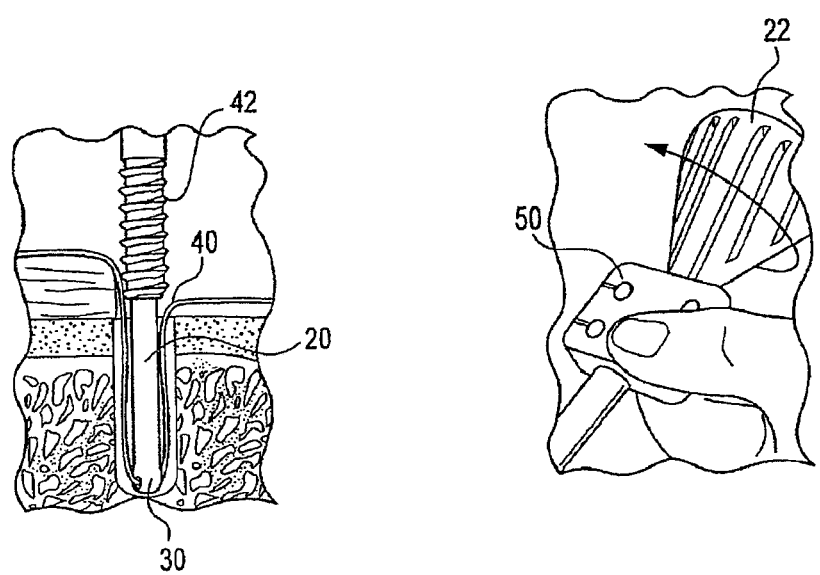
FIG. 4
FIG. 4A

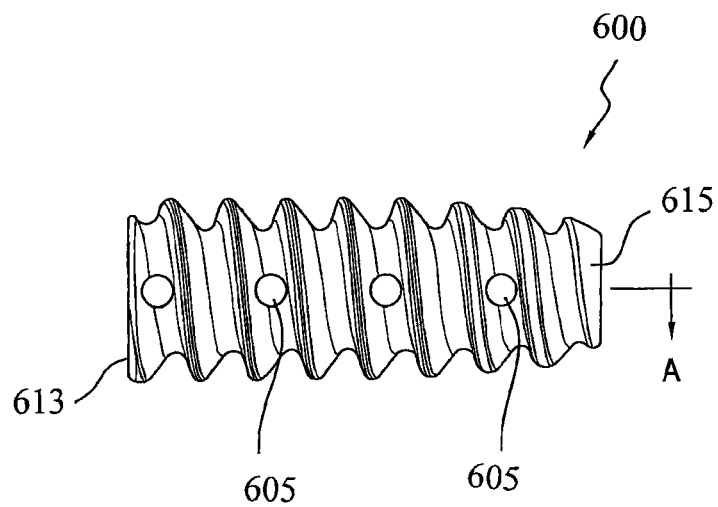
FIG. 14
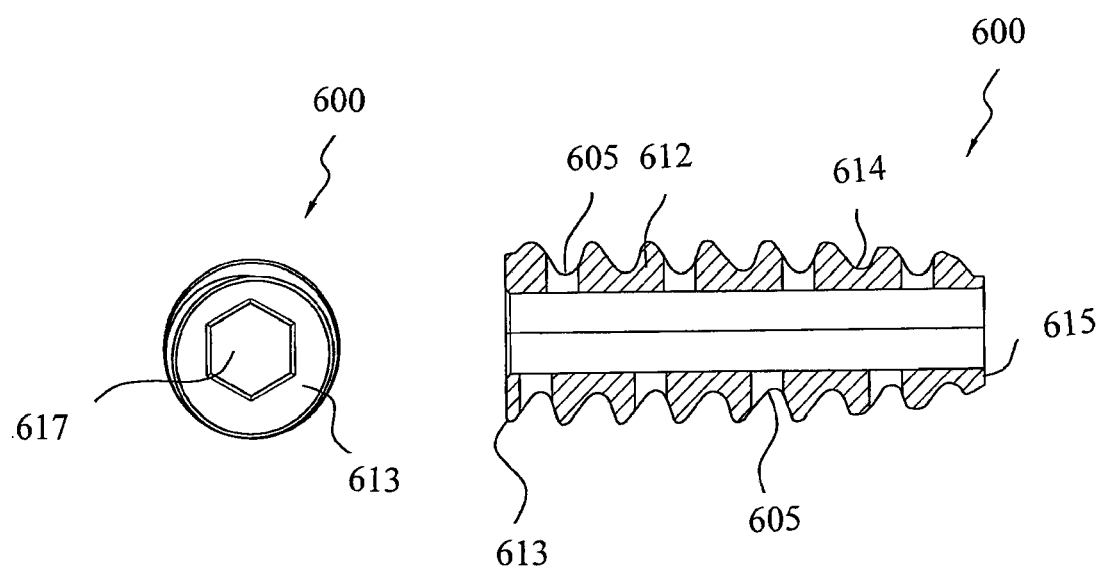
FIG. 15
FIG. 16

SUTURE ANCHOR FOR KNOTLESS FIXATION OF TISSUE

This is a continuation of application Ser. No. 15/976,157, filed May 10, 2018, which is a continuation of application Ser. No. 14/707,861, filed on May 8, 2015, now U.S. Pat. No. 10,881,388, which is a continuation of application Ser. No. 13/403,366, filed Feb. 23, 2012, now abandoned, which is a continuation of application Ser. No. 12/418,391, filed on Apr. 3, 2009, now abandoned, which is a continuation-in-part of application Ser. No. 12/368,946, filed on Feb. 10, 2009, now abandoned, which is: (i) a continuation-in-part of application Ser. No. 12/043,008, filed on Mar. 5, 2008, now abandoned, which in turn is a continuation-in-part of application Ser. No. 11/802,057, filed on May 18, 2007, now U.S. Pat. No. 9,005,246, which claims the benefit of Provisional Application No. 60/801,097, filed on May 18, 2006; and (2) a continuation-in-part of application Ser. No. 11/392,798, filed on Mar. 30, 2006, now U.S. Pat. No. 7,803,173, which claims the benefit of Provisional Application No. 60/666,518, filed on Mar. 30, 2005. The entire disclosures of all of these priority applications are incorporated herein by reference.

FIELD OF THE INVENTION

The present invention relates to methods and instruments for fixation of sutures and tissue to bone.

BACKGROUND OF THE INVENTION

When soft tissue tears away from bone, reattachment becomes necessary. Various devices, including sutures, screws, staples, wedges, anchors and plugs have been used in the prior art to secure soft tissue to bone. Surgical methods utilizing suture anchors alone are disadvantageous for reattachment of large areas of detached tissue because they often do not allow good tissue to bone contact.

Reattachment of soft tissue to bone typically requires the surgeon to pass suture material through selected tissue, form a plurality of surgical knots extracorporeally and then move the knots into position adjacent the desired tissue to be sutured. In such procedures, the surgeon must manually tie the knots on the suture strands after the suture is threaded through the selected tissues to be sutured. Knot tying during surgery, particularly arthroscopic surgery, is tedious and time-consuming. There is also a tendency for the knots to deform or collapse as the surgeon manually forces the knots down into the proper position. Also, the suture knots often are exposed to abrasion or cutting by sharp or rough areas along the walls of the bone canal into which anchors are typically inserted to provide fixation of tendon to bone.

Accordingly, a need exists for an improved method for attaching soft tissue to bone which does not require multiple suture knots and which allows the tendon to remain securely in place until the ligaments naturally attach to bone. A need also exists for such a knotless method of attaching tissue to bone which employs an implant with a fenestrated configuration that promotes healing of tissue.

SUMMARY OF THE INVENTION

The instruments and methods of the present invention overcome the disadvantages of the prior art, such as those noted above, by providing an implant at the distal end of a driver that securely engages and locks into a cannulated interference plug or screw. The implant receives a strand attached to a graft.

In one embodiment of the invention, the strand is passed through the graft at desired points. A cannulated plug or screw is pre-loaded onto a driver provided with a swivel lock twist-in anchor at its distal end. The strand attached to the graft is passed through an aperture of the implant, which is located at the distal end of the driver. The distal end of the driver together with the implant is inserted directly into the bone. The driver may be rotated (in a clockwise direction, for example) to advance a screw over the anchor to complete insertion.

Other features and advantages of the present invention will become apparent from the following description of exemplary embodiments of the invention described with reference to the accompanying drawings.

BRIEF DESCRIPTION OF THE DRAWINGS

FIGS. 1-6 depict a series of steps of shoulder repair using a plurality of swivel anchor devices according to the present invention.

FIGS. 14-16 illustrate various views of a fixation device with fenestrations and used in conjunction with the swivel anchor assembly of the present invention.

DETAILED DESCRIPTION OF THE PREFERRED EMBODIMENTS

The present invention provides apparatus and methods for knotless tissue fixation using a swivel anchor device.

Figure 1:
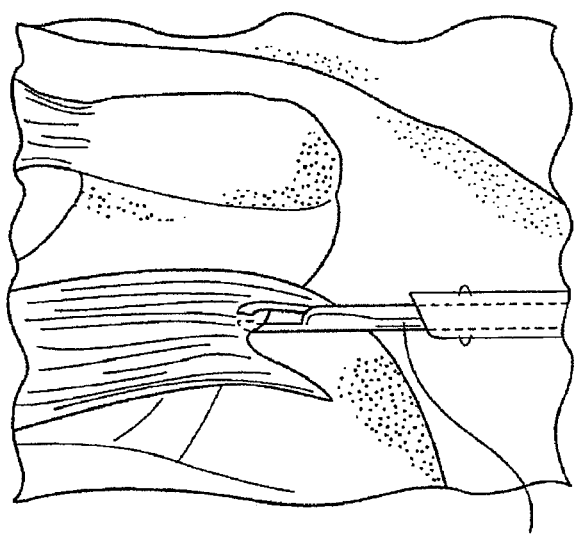

FIG. 1 illustrates a side view of a human shoulder of a patient undergoing a rotator cuff repair in accordance with an exemplary embodiment of the present invention. The patient may be positioned in the beach chair position using the Arthrex Beach Chair Lateral Traction Device or in a lateral decubitus position using the Arthrex 3-Point Shoulder Distraction System. Access to the subacromial space is facilitated with a variety of cannulas.

First, and as illustrated in FIG. 1, the mobility of the tear is assessed using, for example, a tissue grasper 10 such as the Arthrex KingFisher™ Suture Retriever/Tissue Grasper, to determine whether a U or L-shaped component exists. Where large tears extend to the superior aspect of the glenoid, margin convergence suturing is performed to reduce volume and strain on the repair. Subsequently, the length and width of the rotator cuff footprint is assessed and a bleeding bed for enhanced tendon to bone healing may be formed. This may be accomplished with a burr to perform a light dusting of the greater tuberosity, or by using a chondro pick to microfracture the footprint and maximize vascular channels.

Figure 2:
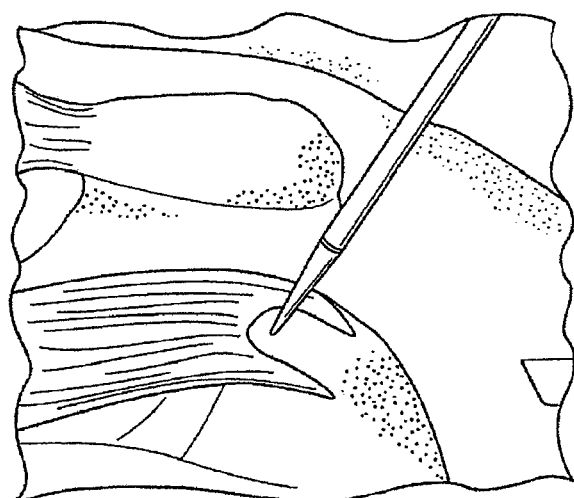

FIG. 2 illustrates the preparation of two pilot holes for two swivel anchors that will be inserted in the medial row. A punch may be employed adjacent to the articular margin of the humerus and at about 45° angle to form the two pilot holes.

Subsequent to the formation of the pilot holes, and as shown in FIGS. 3 and 4, a swivel implant 30, loaded with a strand of suture tape 40, preferably Arthrex FiberTape, is placed in the medial pre-formed hole 32. Arthrex FiberTape is a high strength suture tape which is braided and rectangular-like in cross section and is disclosed in U.S. Pat. No. 7,892,256, the disclosure of which is incorporated by reference herein. However, the anchor of the present invention can be used with any type of flexible material or suture. The driver is then rotated to advance screw 42 down shaft 20 to secure the implant and suture in the bone hole. More specifically, as shown in FIG. 4A, the screw 42 is advanced by holding thumb pad 50 as the driver handle 22 is turned clockwise. An Arthrex FiberLink and an Arthrex Scorpion suture passer 44, are used to shuttle both tails of the suture tape through the rotator cuff 34 simultaneously. This procedure is followed for both medial swivel anchors.

Figure 5:
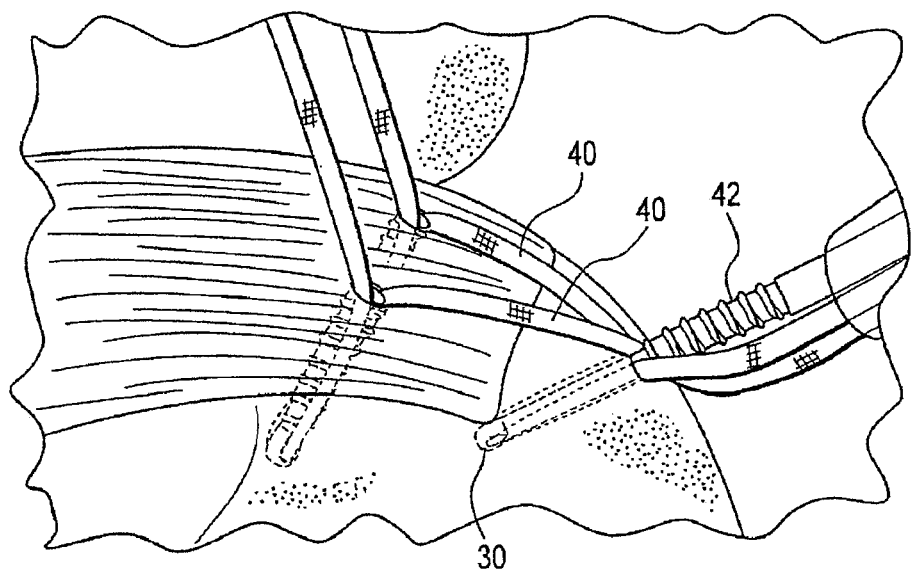
Figure 6:
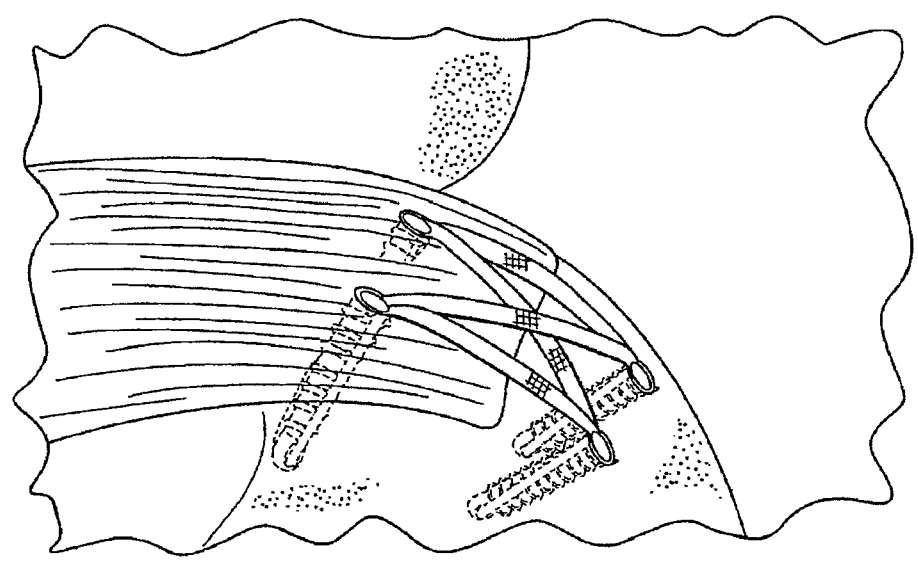
Figure 12:
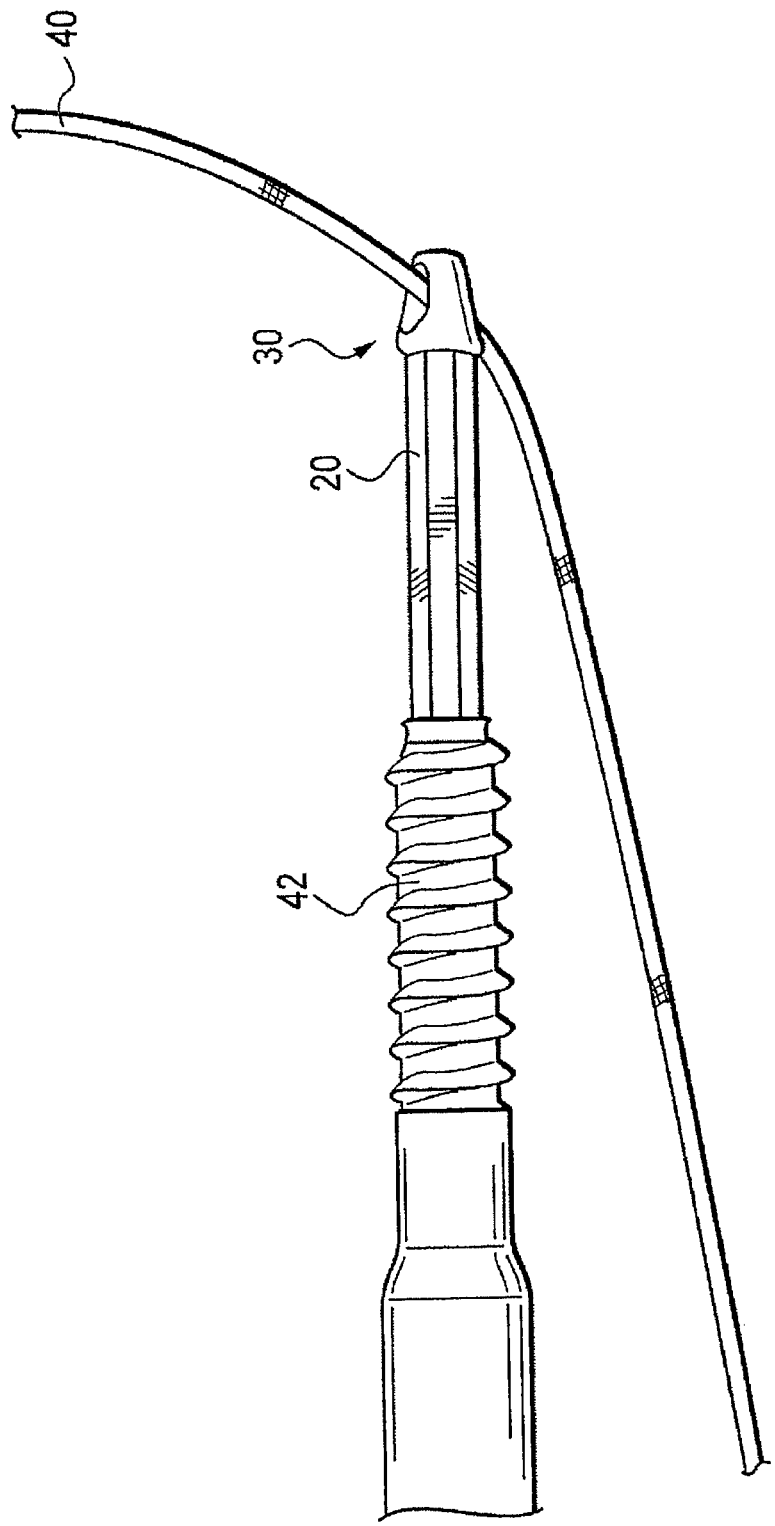
FIGS. 12 and 13 provide additional illustrations of the swivel anchor assembly of the present invention, and the swivel anchor inserted in a bone socket, respectively.
Figure 13:
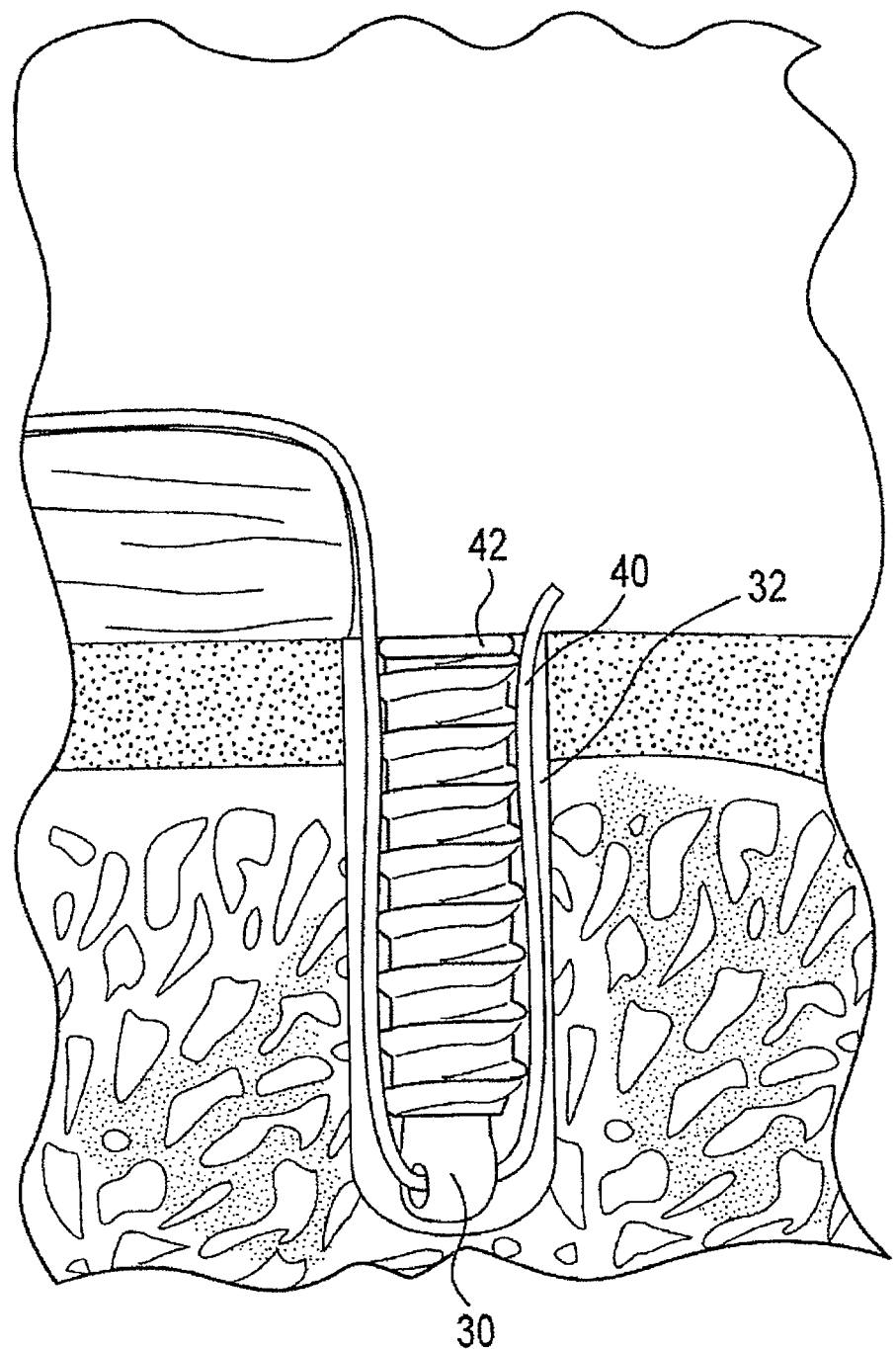

Referring to FIG. 5, one tail of suture tape 40 from each medial swivel anchor is retrieved and loaded through the eyelet of another swivel implant 30, and that implant is installed in then inserted into a preformed lateral bone socket. The tension of the suture tape 40 is adjusted if necessary. The swivel anchor driver is then rotated in clockwise direction as before to advance the screw 42 over the implant to complete insertion. This step is repeated in another lateral bone socket with the other tails of suture tape from each medial anchor. The tails of the suture tape 40 are then cut, one at a time, to complete the construct as shown in FIG. 6. The method is analogous to the method disclosed in U.S. Pat. No. 8,012,174, the entire disclosure of which is incorporated by reference herein. FIGS. 12 and 13 provide additional illustrations of the swivel anchor assembly and the anchor inserted in a bone socket, respectively.

Figure 10:
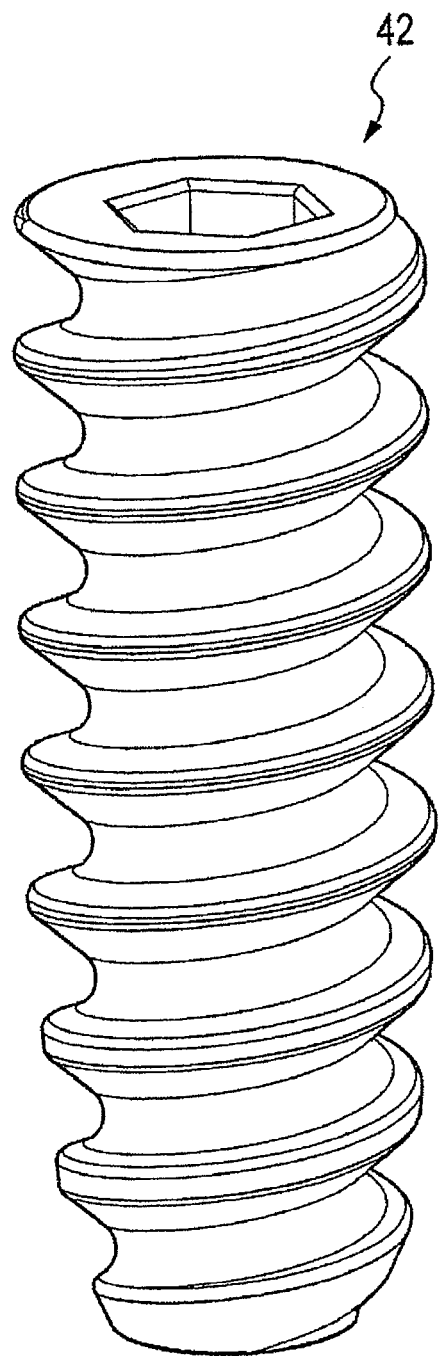
FIG. 10 is an enlarged view of the fixation device (cannulated screw) used in the present invention.
Figure 11A:
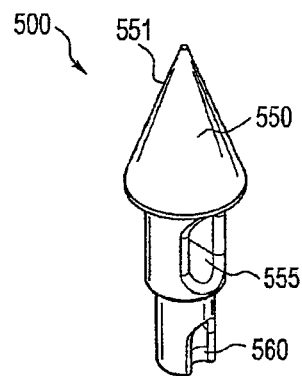
FIGS. 11A-11E illustrate various views of a swivel anchor with a metal tip which avoids the need to pre-drill a hole in bone.
Figure 11B:
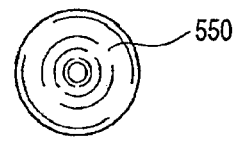
Figure 11C:
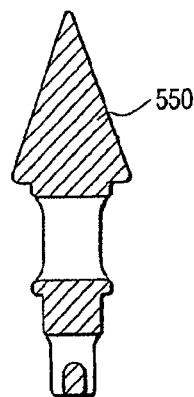
Figure 11D:
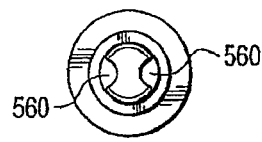
Figure 11E:
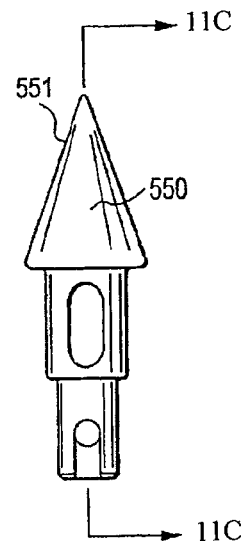

The swivel anchor and instruments of the present invention are now described in greater detail. As shown in FIGS. 7A-7F, a driver 68 is used to install the knotless fixation devices with a swiveling implant. Driver 68 features a thin cannulated rod 20 passing slidably and rotatably through a cannulated driver assembly. The tip of thin cannulated rod 20 is adapted to accept swivel anchor implant 42 within the cannulation at its tip, preferably via a snap fit. Cannulated rod 20 has a hexagonal outer surface for receiving anchor body (preferably a screw) 42 having a corresponding cannulation. FIG. 10 illustrates a detailed view of the cannulated screw 42.

Figure 7A:
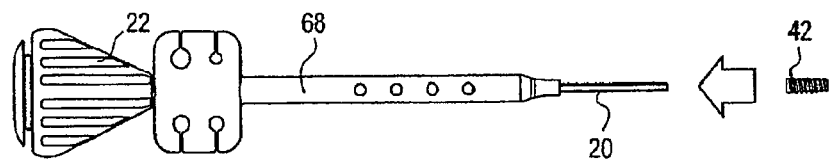
FIGS. 7A-7G illustrate various views of the driver assembly of the present invention.
Figure 7B:
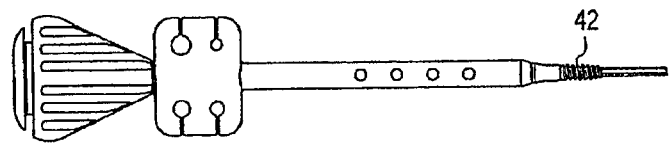
Figure 7C:
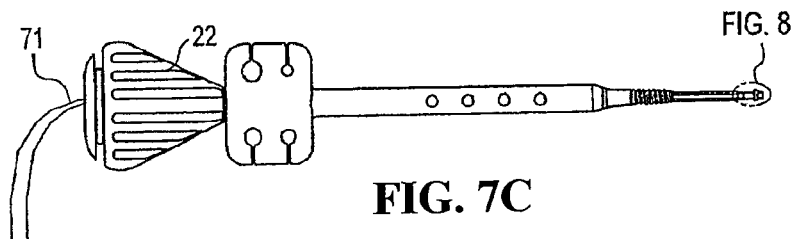
Figure 7D:
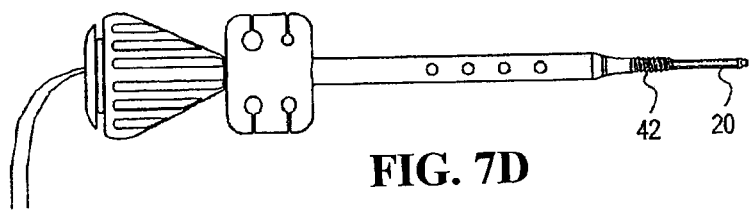
Figure 7E:
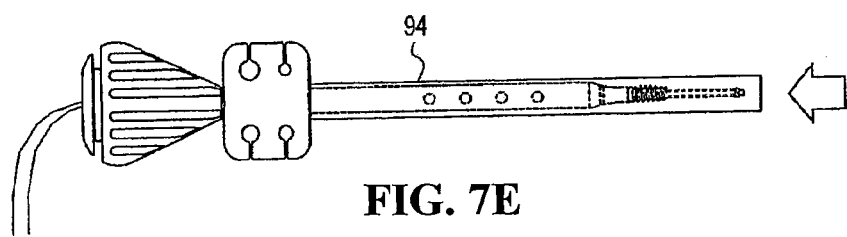
Figure 7F:
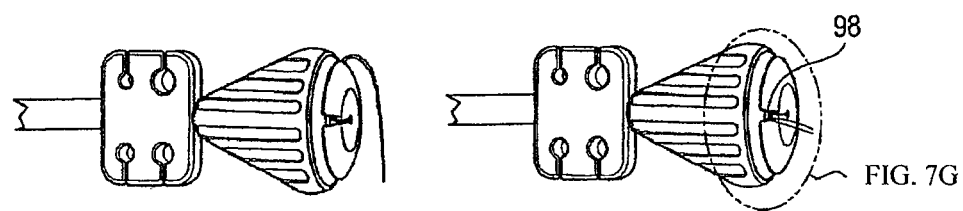
Figure 7G:
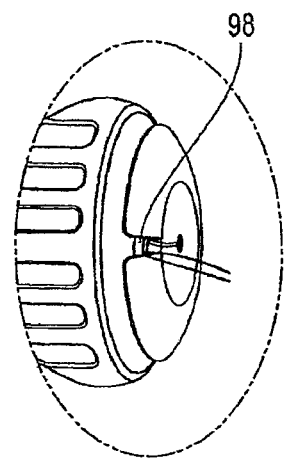
Figure 8:
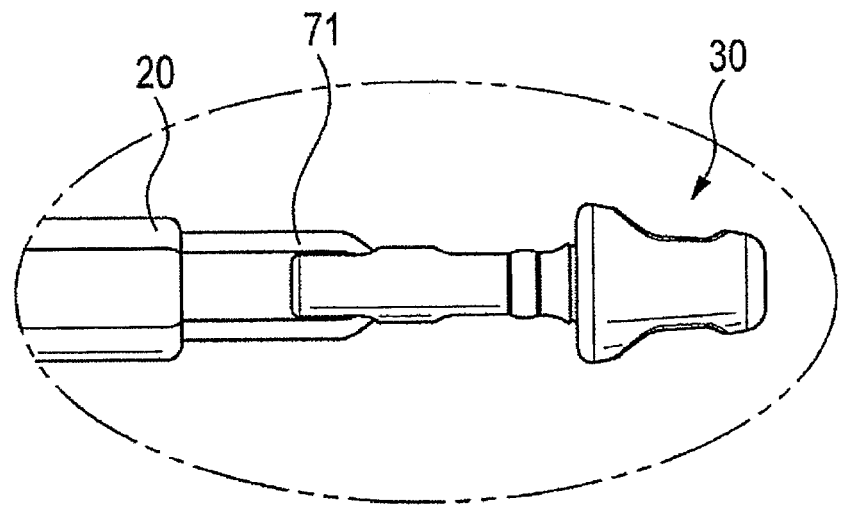
FIGS. 8 and 9 illustrate the swivel implant and traction suture.
Figure 9:
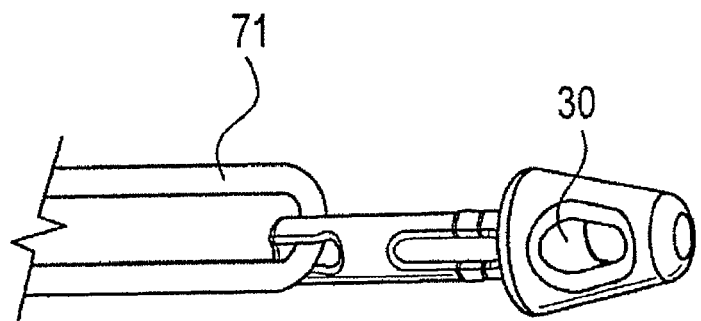

During installation of the knotless anchor having a swiveling implant 30, the screw 42 is first inserted onto cannulated rod 20 of the driver 68. As shown in FIGS. 7A and 7B, screw 42 is loaded onto rod 20 and then fully seated on the shaft end of the driver. FIG. 7C illustrates the swivel anchor implant 30. As shown in FIGS. 8-9, traction sutures 71 extending from the proximal end of the swivel anchor implant 30 are threaded through the cannulation of the driver 68 (see also FIG. 7C). These traction sutures 71 prevent inadvertent separation of the implant 30 from the driver during insertion, but they can be used subsequently for additional tie-down of the tendon after the driver is removed. Subsequently, the swivel anchor implant 30 is seated on the driver tip and until advanced until it snaps onto place (FIG. 7D). A protective tube 94 (FIG. 7E) may be placed over the tip of the assembly for shipping purposes. The traction sutures 71 may be looped around the driver handle, as shown in FIGS. 7F and 7G, and secured in a cleat 98 to prevent the implant 200 from becoming prematurely detached from the driver.

The knotless fixation device of the present invention advantageously minimizes or eliminates the need to tie knots. The use of such a swivel anchor also provides secure fixation of the suture construct—the secure suture construct results from the suture being pushed into a hole and held tightly by an anchors.

In the preferred embodiment of the present invention, as mentioned above, suture tape is used with the swivel anchor to fix tissue to bone. However, the swivel anchor of the present invention can be used with any type of flexible material or suture. In another preferred embodiment, an allograft or biological component may be used instead of suture or tape. The allograft or biological component may be comprised of tendon or pericardium, for example, which provides improved tissue repair. In yet additional embodiments, any combination of suture, suture tape, and allograft or biological component may be employed, depending on the characteristics of the specific surgical repair and/or as desired.

FIGS. 11A-11E illustrate a swivel implant 500 which is provided with a pointed metal tip to facilitate insertion of the implant without the need to pre-drill or pre-form a hole in the bone. The conical configuration of the most distal end pointed tip 550 allows the implant to undergo a self-punching operation, eliminating any need to pre-drill a hole in the bone. The conical configuration of the most distal end of the pointed tip implant 550 also provides suture fixation strength, as well as accelerated graft/tendon healing to bone. The pointed tip implant 550 may be detachable from the driver.

As illustrated in FIGS. 11A-11E, pointed tip implant 500 is provided with a metal tip 550 and an eyelet or aperture 555 for receiving suture or suture tape. Pointed tip implant 550 is also provided, at its most distal end, with a conical portion 551 which allows direct advancement of the implant (by simply tapping the device with a mallet, for example) without the formation of a pilot hole in bone. Preferably, the conical portion 551 of the implant is formed of titanium or titanium alloy. In a preferred embodiment, eyelet or aperture 555 is also formed of titanium or similar material, to withstand impaction forces during the graft fixation procedure.

FIGS. 14-16 illustrate various views of another exemplary fixation device 600 of the present invention that is employed in conjunction with the driver assembly 68 and a swivel anchor or implant of the present invention (such as the swivel anchor implant 30 or the swivel implant 500 described above). The fixation device 600 is similar to the fixation device (swivel anchor implant) 42 of FIG. 10, but differs from it in that the fixation device 600 is provided with a plurality of openings or fenestrations 605 provided on the outer surface of the body of the device. The openings or fenestrations 605 may have various dimensions and geometries provide multiple pathways for w blood to pass through the device (i.e, through the fenestrations and up through the cannulation) and, therefore, to the repair site to promote healing. The fenestrations also promote in-growth of bone. The decreased mass of the device 600 (resulting from the fenestrations) further promotes healing and in-growth.

Preferably, the fixation device 600 is preloaded on the driver 68. As described above with reference to the three exemplary embodiments, the fixation device 600 is advanced into the bone socket by holding the thumb pad 50 as the driver handle 22 is turned clockwise. When the fixation device 600 is fully seated, the shaft of the anchor implant 30 or the swivel implant 500 is fully engaged by the fixation device 600 to optimize the stability of the swivel anchor construct (composed of swivel anchor or implant 30, 500 and fixation device 600).

As illustrated in FIGS. 14-16, the fixation device 600 includes a cannulated body 612 in the form of a tapered cylinder having a proximal end 613 and a distal end 615. A continuous thread 620 wraps around cannulated body 612 in a clockwise direction, as shown. As shown in FIG. 15, the distal end 615 of the interference screw 600 terminates in an exposed, flat surface provided with an opening 616. The proximal end 613 of the interference screw 600 terminates in a drive socket 617 that allows a driver to seat snuggly in the drive socket to allow manipulation and installation of the interference screw into the bone socket, while fully engaging the shaft of the swivel anchor 30 or swivel implant 500 (as detailed above with reference to interference screw 42). As shown in FIG. 16, drive socket 617 may be configured to be used with a traditional hex drive screwdriver. Although the drive socket 617 has been described as having hexagonal shape, the drive socket may also have a Delta drive configuration or a cruciform shape, among others, that allows the driver to rotationally engage the interference screw, to turn simultaneously with the driver.

The fixation device 600 of the present invention may be formed of a biocompatible and/or biosorbable material. Preferably, screw 600 is formed of a bioabsorbable material, such as poly-(L-lactic acid) (PLLA), poly-(D,L-lactide), and poly glycolic acid (PGA), for example, or other bioabsorbable, non-metallic materials, which may be especially tailored for hardness, tensile strength and compressive strength. Alternatively, fixation device 600 may be formed of titanium, titanium alloy, stainless steel or stainless steel alloy. Other biocompatible materials which could be used include plastics, allograft bone and inert bone substitute materials.

A growth material may be advanced through the cannulated driver and into the screw 600 by employing a plunger, for example. As the driver is pulled out, the plunger pushes the flow material through the cannulation of the driver and into the body of the screw 600. The growth material will subsequently harden to allow better fixation of the interference screw 600 against the bone and the shaft of the swivel anchor 30 or swivel implant 500.

The growth material may be any solid, semi-solid, viscous, flowable, gel or elastic composition or mixture that allows its easy manipulation and insertion into the body 612 of the interference screw 600. The growth material may contain growth factors such as autogenous growth factors, for example platelet-rich plasma (PRP), optionally in combination with hyaluronic acid (HY acid) and/or with a coagulant such as thrombin.

The term "growth factor" as used in the present application is intended to include all factors, such as proteinaceous factors, for example, which play a role in the induction or conduction of growth of bone, ligaments, cartilage or other tissues associated with bone or joints. In particular, these growth factors include bFGF, aFGF, EGF (epidermal growth factor), PDGF (platelet-derived growth factor), IGF (insulin-like growth factor), TGF-β. I through III, including the TGF-β. superfamily (BMP-1 through 12, GDF 1 through 12, dpp, 60A, BIP, OF).

Optionally, the growth material may comprise additional osteoconductive bone adhesives, calcium carbonate, fatty acids, lubricants, antiseptic chemicals and/or antibiotics. In this case, other solution excipients such as buffer salts, sugars, anti-oxidants and preservatives to maintain the bioactivity of the growth material and a proper pH of the growth material may be also employed. The additional lubricants and/or the antiseptic and/or the antibiotic will typically be present in the growth material in a predetermined concentration range, which will be dependent upon the particular bone site and application, as well as the specific activity of the antiseptic and/or the antibiotic.

Although the present invention has been described in relation to particular embodiments thereof, many other variations and modifications and other uses will become apparent to those skilled in the art. It is preferred, therefore, that the present invention be limited not by the specific disclosure herein.

What is claimed is:

1. A knotless suture anchor assembly, comprising:
   an inserter comprising a cannulated driver assembly having a distal end and a rod passing slidably through the driver assembly;
   an implant disposed at a distal end of the rod; and
   a screw disposed on the rod, wherein the inserter is engageable with the screw and is configured to rotate the screw with respect to the implant;
   wherein the implant is configured to hold a flexible member for implantation into bone,
   wherein the implant and the screw are configured to be held in place axially using the inserter until advancement of the screw in a distal direction,
   wherein the cannulated driver assembly and the rod are movable relative to one another to rotate and advance the screw axially into a hole in the bone, toward the implant, and
   wherein the implant comprises an abutment surface which abuts against a distal surface of the screw when the screw is rotationally advanced axially toward the implant.

2. The knotless suture anchor assembly of claim 1, wherein the driver assembly includes a handle and a thumb pad.

3. The knotless suture anchor assembly of claim 2, wherein the rod is connected to the thumb pad to maintain a rotational orientation of the implant and a portion of the flexible member captured by the implant in the hole in bone, as the screw is rotated and advanced axially.

4. The knotless suture anchor assembly of claim 1, wherein the screw is movable axially relative to the rod, and wherein a portion of the inserter is configured to be rotationally fixed with the screw.

5. The knotless suture anchor assembly of claim 1, wherein the implant comprises an opening for capturing the flexible member.

6. The knotless suture anchor assembly of claim 1, wherein the flexible member comprises suture.

7. The knotless suture anchor assembly of claim 1, wherein the abutment surface is flat.

8. The knotless surgical anchor assembly of claim 1, wherein the screw is a non-expandable fixation device.

9. A knotless suture anchor assembly, comprising:
   a knotless suture anchor comprising a screw and an implant, wherein the implant is configured to capture a flexible member for implantation into bone; and
   an inserter for facilitating implantation of the screw and the implant into a hole in the bone, the inserter comprising:
   a rod configured to releasably engage the implant, and a cannulated driver assembly arranged such that the rod passes at least partially through the cannulated driver assembly, wherein the inserter is engageable with the screw and is configured to rotate the screw with respect to the implant and advance the screw axially into the hole in the bone, towards the implant, and wherein the implant comprises an abutment surface which abuts against a distal surface of the screw when the screw is rotationally advanced axially toward the implant.

10. The knotless suture anchor assembly of claim 9, wherein the screw is axially movable relative to the rod, and wherein a portion of the inserter is configured to be rotationally fixed with the screw.

11. The knotless suture anchor assembly of claim 10, wherein the screw is cannulated, and wherein a cross-sectional profile of the portion of the inserter corresponds with a cross-sectional profile of the cannulation of the screw to fix a rotational orientation of the screw relative to the rod.

12. The knotless suture anchor assembly of claim 9, wherein the rod is connected to a thumb pad to maintain a rotational orientation of the implant and a portion of the flexible member captured by the implant in the hole in bone, as the screw is rotated and advanced axially.

13. The knotless suture anchor assembly of claim 9, wherein the implant comprises an opening for capturing the flexible member.

14. The knotless suture anchor assembly of claim 9, wherein the flexible member comprises suture.

15. The knotless suture anchor assembly of claim 9, wherein the abutment surface is flat.

16. The knotless suture anchor assembly of claim 9, wherein when the implant and the screw have been fully implanted into the hole in bone, the entire implant remains distal to a proximal end of the screw in the hole.

17. The knotless suture anchor assembly of claim 9, further comprising a traction suture extending from the implant and threaded through the cannulation of the driver assembly.

18. The knotless surgical anchor assembly of claim 9, wherein the screw is a non-expandable fixation device.

19. The knotless surgical anchor assembly of claim 9, wherein the inserter separately engages the screw and the implant, respectively.

20. The knotless suture anchor assembly of claim 9, further comprising at least one other flexible member extending from the implant and passing through the cannulation of the driver assembly.

21. The knotless suture anchor assembly of claim 20, wherein the at least one other flexible member is removable after insertion of the implant and the screw into bone.

22. The knotless suture anchor assembly of claim 20, wherein the at least one other flexible member is coupled to the implant proximal to a location where the flexible member is captured by the implant.

* * * * *